US00PP37651P2

(12) United States Plant Patent
van Swieten

(10) Patent No.: US PP37,651 P2
(45) Date of Patent: Aug. 25, 2026

(54) ***PHALAENOPSIS* PLANT NAMED 'PHA958054'**

(50) Latin Name: *Phalaenopsis hybrida*
Varietal Denomination: PHA958054

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/329,332

(22) Filed: Sep. 15, 2025

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP25,294 P3 * 2/2015 Van Rosmalen ..... A01H 5/02
Plt./311

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'PHA958054', characterized by its compact and upright plant habit; moderately vigorous and moderate growth rate; strong flowering stems; freely flowering habit with typically two inflorescences developing per plant, each inflorescence with numerous flowers; narrow reddish purple-colored flowers with narrow white to light pale purple-colored marginal edges and dark red to purplish red-colored labella; and good postproduction longevity.

2 Drawing Sheets

Figure 1:
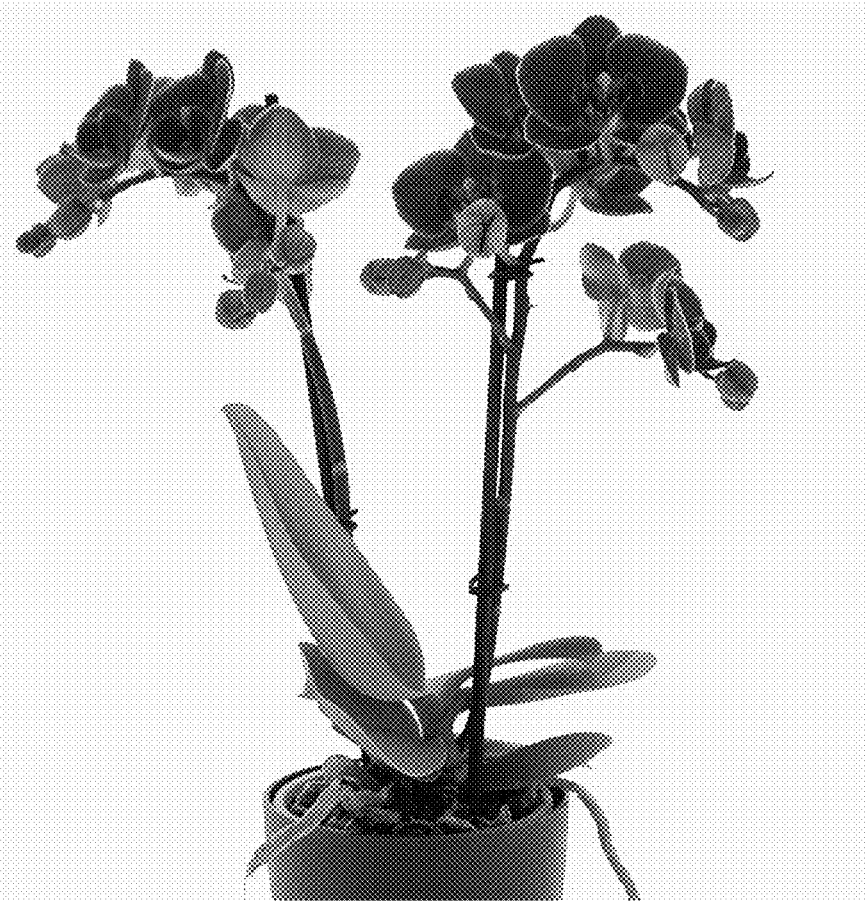

Botanical designation: *Phalaenopsis hybrida.*
Cultivar denomination: 'PHA958054'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B. V. of Bleiswijk, The Netherlands on Dec. 30, 2024, application number 2024/3262. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA958054'.

The new *Phalaenopsis* plant is a product of a planned breeding program conducted by the Inventor in Bleiswijk, The Netherlands. The objective of the breeding program is to develop new freely flowering *Phalaenopsis* plants with reddish purple-colored flowers.

The new *Phalaenopsis* plant originated from a cross-pollination in August, 2016 in Bleiswijk, The Netherlands of a proprietary breeding selection of *Phalaenopsis hybrida* identified as code number 13-055338-0006, not patented, as the female, or seed, parent with a proprietary breeding selection of *Phalaenopsis hybrida* identified as code number 13-054575-0009, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in August, 2019.

Asexual reproduction of the new *Phalaenopsis* plant by in vitro meristem propagation in a controlled environment in Bleiswijk, The Netherlands since August, 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA958054'. These characteristics in combination distinguish 'PHA958054' as a new and distinct *Phalaenopsis* plant:

1. Compact and upright plant habit.
2. Moderately vigorous and moderate growth rate.
3. Strong flowering stems.
4. Freely flowering habit with typically two inflorescences developing per plant, each inflorescence with numerous flowers.

5. Narrow reddish purple-colored flowers with narrow white to light pale purple-colored marginal edges and dark red to purplish red-colored labella.
6. Good postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are horizontal to semi-erect in aspect whereas leaves of plants of the female parent selection are erect to semi-erect in aspect.
2. The lateral lobes of the labella of plants of the new *Phalaenopsis* are larger than the central lobe whereas the lateral lobes of the labella of plants of the female parent selection are equal in size to the central lobe.
3. Flower petals of plants of the new *Phalaenopsis* do not have any spots whereas flower petals of plants of the female parent selection are spotted.

Plants of the new *Phalaenopsis* can be compared to plants of the male parent selection. Plants of the new *Phalaenopsis* differ primarily from plants of the male parent selection in plant size as plants of the new *Phalaenopsis* are shorter than plants of the male parent selection.

Plants of the new *Phalaenopsis* can be compared to plants of *Phalaenopsis hybrida* 'PHALDIMXAP', disclosed in U.S. Plant Pat. No. 25,294. In side-by-side comparisons, plants of the new *Phalaenopsis* differ primarily from plants of 'PHALDIMXAP' in the following characteristics:

1. Leaves of plants of the new *Phalaenopsis* are horizontal to semi-erect in aspect whereas leaves of plants of 'PHALDIMXAP' are horizontal in aspect.
2. Leaves of plants of the new *Phalaenopsis* have acute to broadly acute apices whereas leaves of plants of 'PHALDIMXAP' have obtuse apices.
3. Flower petals of plants of the new *Phalaenopsis* are reddish purple in color whereas flower petals of plants of 'PHALDIMXAP' are purple in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA958054' grown in a container.

Figure 2:
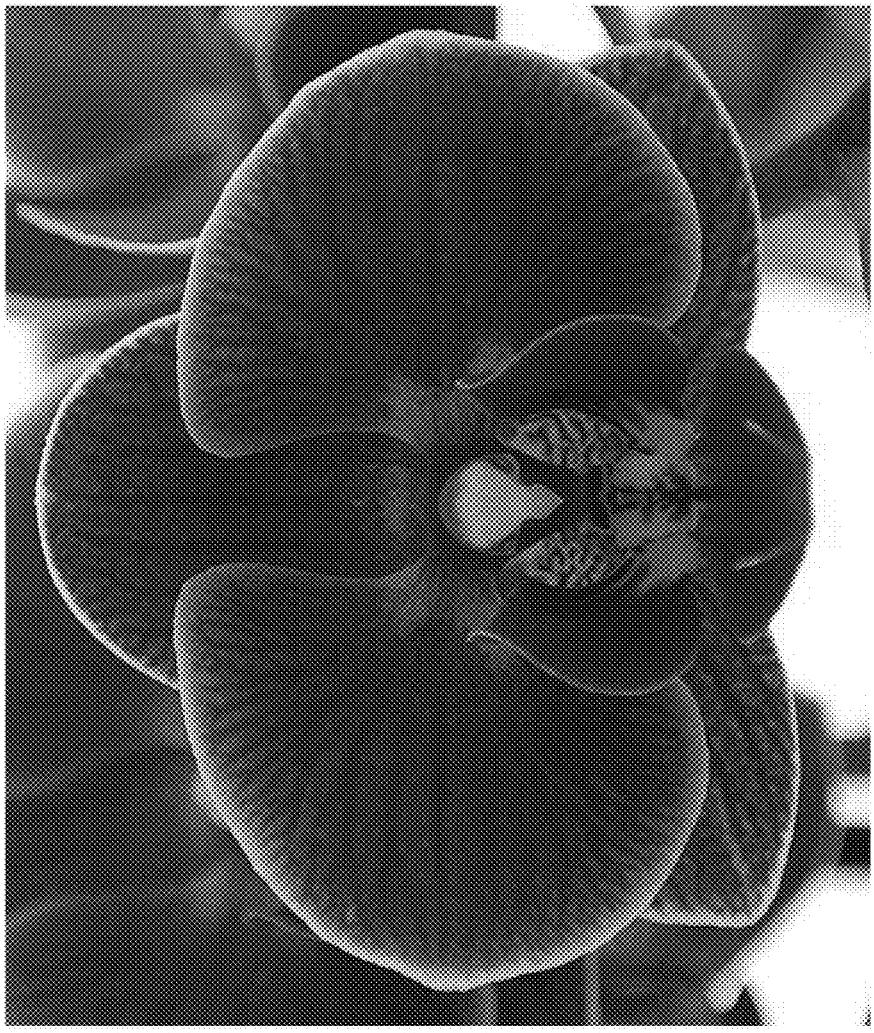

The photograph on the second sheet (FIG. 2) is a close-up view of a typical flower of 'PHA958054'.

DETAILED BOTANICAL DESCRIPTION

The aforementioned photographs and following observations and measurements describe plants grown during the summer in 9-cm containers in a glass-covered greenhouse in Bleiswijk, The Netherlands and grown under cultural practices typically used in commercial *Phalaenopsis* production. Plants were 16 months old when the photographs and description were taken. During the first 13 months of production of the plants, day and night temperatures averaged 28.5° C., and during the last three months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA958054'.

Parentage:

*Female, or seed, parent*.—Proprietary breeding selection of *Phalaenopsis hybrida* identified as code number 13-055338-0006, not patented.

*Male, or pollen, parent*.—Proprietary breeding selection of *Phalaenopsis hybrida* identified as code number 13-054575-0009, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; compact and upright plant habit; typically two inflorescences developing per plant, each inflorescence with numerous flowers; monopodial; moderately vigorous growth habit and moderate growth rate.

*Plant height, substrate level to top of foliar plane*.—About 10.9 cm.

*Plant height, substrate level to top of floral plane*.—About 22.2 cm.

*Plant diameter or spread*.—About 21.2 cm.

Leaf description:

*Arrangement and quantity*.—Distichous, simple; sessile; about five to six fully-developed leaves per plant.

*Length*.—About 12.4 cm.

*Width*.—About 6.1 cm.

*Aspect*.—Horizontal to semi-erect.

*Shape*.—Elliptic; slightly carinate.

*Apex*.—Unequal acute to unequal broadly acute.

*Base*.—Sheathing. Sheath length: About 1 cm. Sheath width: About 1.1 cm. Sheath color: Close to 144B.

*Margin*.—Entire; not undulate.

*Texture and luster, upper surface*.—Smooth, glabrous; slightly glossy.

*Texture and luster, lower surface*.—Smooth, glabrous; matte

*Venation pattern*.—Camptodromous.

*Color*.—Developing leaves, upper surface: Close to a blend of 144A and 146A. Developing leaves, lower surface: Close to 144A. Fully expanded leaves, upper surface: Close to 146A; venation, close to NN137C. Fully expanded leaves, lower surface: Close to 146B; venation, close to 143B.

Inflorescence description:

*Appearance and flowering habit*.—Showy zygomorphic flowers arranged on axillary simple or branched racemes; typically two inflorescences develop per plant; each inflorescence with about 14 flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about eleven weeks on the plant; flowers not persistent.

*Inflorescence length* (*lowermost flower to inflorescence apex*).—About 13 cm.

*Inflorescence width*.—About 12.7 cm.

*Flower buds*.—Height: About 1.4 cm. Diameter: About 1.1 cm by 1.4 cm. Shape: Broadly ovate. Color: Close to a blend of 145B and 151D; upper surface, close to 186A and 186B; venation, close to 187C.

*Flower size*.—About 4 cm (vertical) by 4.9 cm (horizontal).

*Flower depth*.—About 2.5 cm.

*Petals, quantity and arrangement*.—Three, two lateral petals and one center petal transformed into a labellum.

*Lateral petals*.—Length: About 2.3 cm. Width: About 2.9 cm. Shape: Reniform to close to broadly lunate. Apex: Rounded to slightly acute. Margin: Entire; not undulate. Texture and luster, upper surface: Smooth, glabrous; velvety; matte. Texture and luster, lower surface: Smooth, glabrous; moderately velvety; matte. Color: When opening, upper surface: Close to NN78A; narrow marginal edges, close to N155A; at the base, close to N75A and N75B; venation, close to a blend of N78A and N79C. When opening, lower surface: Close to 72B; narrow marginal edges, close to N155A; towards the center and base, close to N75A and N75B; venation, close to 72A. Fully opened, upper surface: Close to NN78A; narrow marginal edges, close to 84D; at the base, close to N75B; venation, close to N78A; colors do not change with subsequent development. Fully opened, lower surface: Close to N78B; narrow marginal edges, close to 84D; towards the center and base, close to N75D and N76A; venation, close to N78A; colors do not change with subsequent development.

*Labella*.—Appearance: Three-parted with two lateral lobes and a central lobe; overall shape, broadly cordate to reniform. Length, lateral lobes: About 1.5 cm. Width, lateral lobes: About 1 cm. Length, central lobe: About 1.6 cm. Width, central lobe: About 3 mm to 15 mm. Length, cirrhose tips: About 4 mm. Shape, lateral lobes: Broadly obovate. Shape, central lobe: Broadly ovate with a slightly elongated apex. Apex, lateral lobes: Obtuse. Apex, central lobe: Cleft with two cirrhose apices, pointing upwards and backwards. Margins, lateral and central lobes: Entire. Texture and luster, lateral and central lobes, upper and lower surfaces: Smooth, glabrous; moderately velvety; matte. Callosities: Located at the base of the labellum and attachment point of the lateral petals; about 4 mm in length, about 4.5 mm in width and about 4 mm in height. Color: When opening, upper surface: Lateral lobes: Close to 59A and 59B; towards the apex, close to N79C; at the base, axial stripes, close to NN155A. Central lobe: Close to 59A; towards the base, close to N79C; at the base, close to N155A with radial stripes, close to 59B and 60A; cirrhose apices, close to N79C and distally, close to 84D. Callosities: Close to NN155C; towards the apex, close to 10A with fine dots, close to 173A. When opening, lower surface: Lateral lobes: Close to 61A; towards the apex, close to 71A; at the base, close to 198C and 198D with axial stripes, close to 71A. Central lobe: Close to 61A; center, close to 84D; towards the base, close to 72A; at the base, close to 156D tinged with close to 163C; cirrhose apices, close to 72A and distally, close to 84D. Fully opened, upper surface: Lateral lobes: Close to 59A and 59B; towards the apex, close to N79C; at the base, axial stripes, close to 155A. Central lobe: Close to 59B; towards the base, close to 71B; at the base, close to N155A with radial stripes, close to 59B and 60A; cirrhose apices, close to 71B and distally, close to 75A. Callosities: Close to NN155A; towards the apex, close to 11A with fine dots, close to 171A. Fully opened, lower surface: Lateral lobes: Close to 61A; towards the apex, close to 71A; at the base, close to 198C and 198D with axial stripes, close to 71A. Central lobe: Close to 61A; center, close to 84D; towards the base, close to 72A; at the base, close to 156D tinged with close to 163C; cirrhose apices, close to 72A and distally, close to 84D.

*Sepals*.—Quantity and arrangement: Three, one upper dorsal sepal and two lower lateral sepals. Length, dorsal sepal: About 2.6 cm. Width, dorsal sepal: About 2.2 cm. Length, lateral sepals: About 2.6 cm. Width, lateral sepals: About 2 cm. Shape, dorsal and lateral sepals: Broadly ovate. Apex, dorsal and lateral sepals: Broadly acute. Base, dorsal and lateral sepals: Cuneate. Margins, dorsal and lateral sepals: Entire; not undulate. Texture and luster, dorsal and lateral sepals, upper surface: Smooth, glabrous; velvety; matte. Texture and luster, dorsal and lateral sepals, lower surface: Smooth, glabrous; moderately velvety; matte. Color, dorsal sepal: When opening, upper surface: Close to 64A; narrow marginal edges, close to N155A; at the base, close to N75A and N75B; venation, close to N79C. When opening, lower surface: Close to 196B and 196C; towards the margins, close to N78B and N78C; narrow marginal edges, close to N155A; venation, close to N79C. Fully opened, upper surface: Close to NN78A; narrow marginal edges, close to 84D; at the base, close to N75B; venation, close to a blend of N79B and N79C. Fully opened, lower surface: Close to 76A and 76B; narrow marginal edges, close to 84D; venation, close to N78B; main color becoming closer to N78C with subsequent development. Color, lateral sepals: When opening, upper surface: Close to 64A; lower half, close to 61A; narrow marginal edges, close to N155A; at the base, close to 151C with fine dots, close to N79B and N79C; venation, close to N79B and N79C. When opening, lower surface: Close to 75C; towards the margins, close to 70B; narrow marginal edges, close to N155A; towards the base, close to 146D; venation, close to 71A. Fully opened, upper surface: Close to NN78A; lower half, close to a blend of 71A and NN78A; narrow marginal edges, close to 84D; towards the base, close to 151D; at the base, fine dots, close to N79B and N79C; venation, close to N79B and N79C. Fully opened, lower surface: Close to 76B; towards the margins, close to 77B; narrow marginal edges, close to 84D; towards the base, close to 145D; venation, close to N78B.

*Peduncles*.—Length: About 23.6 cm. Diameter: About 4 mm. Strength: Strong. Aspect: Upright to outwardly arching. Texture and luster: Smooth, glabrous; matte. Color: Close to 197A; densely covered with fine dots, close to 147C.

*Pedicels*.—Length: About 2.3 cm. Diameter: About 2.75 mm. Strength: Moderately strong. Aspect: About 60° from peduncle axis. Texture and luster: Smooth, glabrous; matte. Color: Close to a blend of 148D and 194C; proximal end, close to N148A; distal end, close to N155C.

*Reproductive organs*.—Androecium: Column length: About 7 mm. Column width: About 5 mm. Column color: Close to NN78B; distally, close to 76C. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to 76D. Ovary length: About 5 mm. Ovary diameter: About 1 mm. Ovary color: Close to 145B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA958054' as herein illustrated and described.

* * * * *